United States Patent [19]

Stahly

[11] Patent Number: 5,003,116
[45] Date of Patent: Mar. 26, 1991

[54] HALOETHYLATION OF AROMATIC HYDROCARBONS

[75] Inventor: Barbara C. Stahly, Baton Rouge, La.

[73] Assignee: Ethyl Corporation, Richmond, Va.

[21] Appl. No.: 419,519

[22] Filed: Oct. 10, 1989

[51] Int. Cl.[5] .............................................. C07C 17/32
[52] U.S. Cl. ..................................... 570/194; 570/195
[58] Field of Search ................ 570/206, 208, 194, 195

[56] References Cited

U.S. PATENT DOCUMENTS

| 2,516,971 | 8/1950 | Galitzenstein et al. | 570/195 |
| 3,006,953 | 10/1961 | Grosskinsky et al. | 570/195 |
| 3,069,480 | 12/1962 | Hirth et al. | 570/195 |
| 3,658,923 | 4/1972 | Stapp | 570/195 |

FOREIGN PATENT DOCUMENTS 0044647  1/1982  European Pat. Off. ............ 570/195

OTHER PUBLICATIONS

March, "Advanced Organic Chemistry", Second Ed. McGraw-Hill, N.Y., (1977), pp. 501–502.
"Friedel–Crafts and Related Reactions", vol. 2, Interscience Publishers, N.Y., (1963–1964), pp. 659–784.

*Primary Examiner*—Werren B. Lone
*Attorney, Agent, or Firm*—Patricia J. Hogan; Richard J. Hammond

[57] ABSTRACT

A monoalkylaromatic hydrocarbon is haloethylated to a 1-halo-1-arylethane with minimal co-formation of diarylalkane by-product by reacting it with hydrogen chloride or bromide and acetaldehyde in the presence of sulfuric acid only until not more than about 60% of the monoalkylaromatic hydrocarbon has been converted.

10 Claims, No Drawings

HALOETHYLATION OF AROMATIC HYDROCARBONS

This invention relates to a process for haloethylating aromatic hydrocarbons to form 1-halo-1-arylethanes.

As disclosed in March, *Advanced Organic Chemistry*, Second Edition, McGraw-Hill, New York, 1977, pp. 501–502; Olah, *Friedel-Crafts and Related Reactions*, Volume 2, Interscience Publishers, New York, 1963–1964, pp. 659–784; U.S. Pat. No. 2,516,971 (Galitzenstein et al.); and the references cited therein, it is known that aromatic compounds can be haloalkylated by reacting them with a hydrogen halide and an appropriate aldehyde in the presence of a Lewis acid or a proton acid as a catalyst, most commonly in the presence of zinc chloride.

The chloroalkylations utilizing formaldehyde as the aldehyde have been successfully employed in providing fairly high yields of 1-chloro-1-arylalkanes; reasonably high yields of 1-chloro-1-arylalkanes have also been obtained from ohloroalkylations utilizing higher aldehydes in some cases, e.g., when the aromatic compound has had an appropriate functional substituent or a plurality of alkyl substituents; and reasonably acceptable, although lower, yields of 1-halo-1-arylalkanes have been obtained in comparable bromoalkylation reactions. However, when the aromatic compound has been a less reactive compound, e.g., an unsubstituted aromatic hydrocarbon or a monoalkylaromatic hydrocarbon, it has not been found possible to provide commercially acceptable yields of 1-halo-1-arylalkane, even when the haloalkylation has been a chloroalkylation rather than a bromoalkylation. There has been too much co-formation of diarylalkane by-product, especially in the bromoalkylation reactions.

1-Halo-1-arylalkanes which it would be particularly desirable to prepare by improved haloalkylation processes are the 1-halo-1-(4- alkylphenyl)alkanes which can be used in known processes, such as those of U.S. Pat. No. 4,536,595 (Gardano et al.), Canadian Patent 1,197,254 (Francalanci et al.), British Patent 1,560,082 (Dynamit Nobel), Czechoslovakian Certificate of Authorship 219,752 (Palecek et al.), and Japanese Kokai 47-39050 (Miyatake et al.) and 52-111536 (Tokutake) to provide ibuprofen and related pharmaceuticals.

Copending application Ser. No. 07/395,017 (Knesel), filed Aug. 17, 1989, teaches that the aforementioned disadvantages of known haloalkylations can be minimized in the haloethylation of monoalkylaromatic hydrocarbons with acetaldehyde and hydrogen chloride or bromide when the reaction is conducted at sufficiently low temperatures in the presence of a sufficient amount of sulfuric acid. However, it would be desirable to make other haloethylation process improvements which could be used instead of or in addition to the improvements taught by Knesel in order to maximize 1-halo-1-arylethane/diarylethane ratios.

It has now been found that the co-formation of diarylalkane by-product formation in the haloethylation of monoalkylaromatic hydrocarbons with acetaldehyde and hydrogen chloride or bromide in the presence of sulfuric acid can be minimized by conducting the reaction to a conversion of monoalkylaromatic hydrocarbon not higher than about 60%.

The aromatic hydrocarbon employed in the practice of the invention is a monoalkylaromatic hydrocarbon, such as 1-methylnaphthalene, 2-methylnaphthalene, 9-methylanthracene, 9-butylanthracene, 9-dodecylanthracene, and the various monoalkylbenzenes, e.g., the methyl-, ethyl-, propyl-, isobutyl-, sec-butyl-, t-butyl-, isopentyl-, t-pentyl-, and hexylbenzenes. The most preferred aromatic hydrocarbons are the monoalkylbenzenes wherein the alkyl group contains 1-5 carbons.

The hydrogen halide which is reacted with the aromatic hydrocarbon and acetaldehyde is preferably anhydrous or at least substantially anhydrous. However, some water in the hydrogen halide can be tolerated as long as it does not provide a degree of dilution such as to necessitate the use of an uneconomically excessive amount of sulfuric acid to compensate for the degree of dilution. The hydrogen halide may be incorporated into the reaction mixture per se or as a salt, such as sodium chloride or bromide, which reacts with sulfuric acid to form hydrogen chloride or bromide under the reaction conditions.

The acetaldehyde may be employed per se or as paraldehyde.

As in Knesel, the teachings of which are incorporated herein in toto by reference, the aromatic hydrocarbon, hydrogen halide, and acetaldehyde may be employed in equimolar amounts; or any of the reactants may be used in amounts which are smaller or larger than the equimolar amounts. However, the use of the acetaldehyde in an amount smaller than the equimolar amount has been found to be of assistance in minimizing the formation of diarylethane and non-aryl by-products.

The sulfuric acid used in the reaction preferably has a concentration of 85–98%, more preferably 88–96%, and most preferably 90–94% to minimize dilution of the catalyst with the consequent need to use more of it. The amount employed is ordinarily such as to provide at least one mol of hydrogen sulfate per mol of acetaldehyde, and it is preferred to provide at least two mols of hydrogen sulfate per mol of acetaldehyde. Unless needed to compensate for considerable dilution of the catalyst, it is seldom used in an amount such as to provide more than about 15 mols of hydrogen sulfate per mol of acetaldehyde.

When the hydrogen halide is hydrogen bromide, the reaction is ordinarily conducted at a temperature in the range of about +10° C. to about −35° C., preferably about 0° C. to about −35° C., in order to maximize the advantages of the invention. When the hydrogen halide is hydrogen chloride, the reaction temperature is ordinarily in the range of about −10° C. to about −35° C.

The process of the invention is exothermic, so the reactants should be combined at a rate that permits control of the reaction temperature. In conducting the process it is preferred to add a mixture of the aromatic hydrocarbon and acetaldehyde to a sulfuric acid solution and sparge the reaction vessel with hydrogen halide throughout the reaction. However, alternatively, the aromatic hydrocarbon can be added to the sulfuric acid, the hydrogen halide flow started, and the acetaldehyde then added slowly; or all ingredients can be added at once.

In accordance with the invention, the process is conducted to a conversion of monoalkylaromatic hydrocarbon not higher then 60% to minimize the co-formation of diarylalkane by-product. Actually, the product/by-product ratio begins to worsen even before the stage of 60% conversion, but it has been found that the best balance of yield and product/by-product ratio is obtained when the conversion is about 30–60%.

The invention is particularly advantageous as a method of preparing 1-halo-1-arylethanes from aromatic hydrocarbons, such as monoalkylbenzenes and other monoalkylaromatic hydrocarbons, that have not previously been found to be capable of providing acceptable yields of such products by haloalkylation processes utilizing acetaldehyde.

As is known, the products obtained by the process are useful as internal standards, intermediates for the preparation of monomers, detergents, pharmaceuticals, etc. When they are used as chemical intermediates, they may be subjected to the same reactions as have previously been used to convert them to desired products. For example, the 1-halo-1-arylethanes can be dehydrohalogenated in any known manner to provide styrenes which can then be polymerized by known techniques.

A particularly interesting application of the 1-halo-1-(4-alkylphenyl)ethanes which are prepared in a preferred embodiment of the invention is as intermediates for the preparation of ibuprofen and related pharmaceuticals. When they are used in such applications, they may be converted to the desired products in any suitable manner. For example, they may be reacted with carbon monoxide in the presence of a carbonylation catalyst to form the corresponding propionic acids as in Gardano et al., Francalanci et al., or Dynamit Nobel; or they may be reacted with an alkali metal cyanide or a tetraalkylammonium cyanide and then hydrolyzed to the corresponding propionic acids as in Palecek et al. or Tokutake. Another useful synthesis involves reacting the compounds with magnesium, carbonating the resultant Grignard reagent with carbon dioxide, and acidifying the carbonated product to the propionic acid as in Miyatake et al.

The following examples are given to illustrate the invention and are not intended as a limitation thereof.

EXAMPLE I

A suitable reaction vessel was charged with 4.0 molar proportions of hydrogen sulfate in the form of 90% sulfuric acid. The acid was cooled to $-16°$ C. to $-21°$ C., a hydrogen chloride sparge was begun, and a solution of 1.2 molar proportions of acetaldehyde in one molar proportion of isobutylbenzene was then added over a period of one hour while stirring the reaction mixture. The stirring, sparging, and maintenance of a temperature of $-16°$ C. to $-21°$ C. were continued for 1.5 hours, after which analyses were made to determine that (1) 37% of the isobutylbenzene had been converted, (2) the yield of 1-chloro-1-(isobutylphenyl)ethane was 29.7%, (3) the yield of 1,1-di(isobutylphenyl)ethane was 6.6%, and (4) the 1-chloro-1-(isobutylphenyl)ethane/-1,1-di(isobutylphenyl)ethane mol ratio was 9.

EXAMPLE II

Example I was essentially repeated except that the initial charge to the reaction vessel was 2.5 molar proportions of hydrogen sulfate in the form of 93.7% sulfuric acid, the temperature was $-16°$ C. to $-26°$ C., and the feed time was 1.2 hours. At the end of the reaction (1) 41% of the isobutylbenzene had been converted, (2) the yield of 1-chloro-1-(isobutylphenyl)-ethane was 32.1%, (3) the yield of 1,1-di(isobutylphenyl)ethane was 7.0%, and (4) the 1-chloro-1-(isobutylphenyl)ethane/1,1-di-(isobutylphenyl)ethane mol ratio was 9.

COMPARATIVE EXAMPLE A

Example II was essentially repeated except that the amount of hydrogen sulfate was increased to 4.0 molar equivalents, the lowest temperature was $-25°$ C., and the feed time was decreased to one hour. At the end of the reaction (1) 68% of the isobutylbenzene had been converted, (2) the yield of 1-chloro-1-(isobutylphenyl)ethane was 46.4%, (3) the yield of 1,1-di(isobutylphenyl)ethane was 17.7%, and (4) the 1-chloro-1-(isobutylphenyl)ethane/1,1-di(isobutylphenyl)ethane mol ratio was only 5.

COMPARATIVE EXAMPLE B

Comparative Example A was essentially repeated except that the amount of hydrogen sulfate was increased to 6.0 molar equivalents. At the end of the reaction (1) 87% of the isobutylbenzene had been converted, (2) the yield of 1-chloro-1-(isobutylphenyl)ethane was 48.7%, (3) the yield of 1,1-di(isobutylphenyl)ethane was 28.8%, and (4) the 1-chloro-1-(isobutylphenyl)-ethane/1,1-di(isobutylphenyl)ethane mol ratio was only 3.

It is obvious that many variations may be made in the products and processes set forth above without departing from the spirit and scope of this invention.

What is claimed is:

1. In a process for haloethylating, a monoalkylbenzene wherein the alkyl group contains 1 to 6 carbon atoms, monomethylnaphthalene or monoalkylanthracne where the alkyl group contains 1 to 12 carbon atoms by reacting it with hydrogen chloride or hydrogen bromide and acetaldehyde at a temperature from about $+10°$ C. to about $-35°$ C. in the presence of hydrogen sulfate so as to provide at least one mole of hydrogen sulfate per mole of acetaldehyde to form a 1-halophenylethane, 1-halonaphthylethane, or 1- haloanthracenylethane; the improvement which comprises minimizing the co-formation of diphenylethane, dinaphthylethane, or dianthracenylethane by-products by conducting the reaction to a conversion of said monoalkylbenzene, monomethylnaphthalene or monoalkylanthracene not higher than about 60%.

2. The process of claim 1 wherein the monoalkylaromatic hydrocarbon is a monoalkylbenzene.

3. The process of claim 2 wherein the monoalkylbenzene is a hydrocarbon in which the alkyl substituent contains 1-5 carbons.

4. The process of claim 3 wherein the monoalkylbenzene is isobutybenzene.

5. The process of claim 1 wherein hydrogen chloride is employed and the reaction temperature is in the range of about $-10°$ C. to about $-35°$ C.

6. The process of claim 1 wherein hydrogen bromide is employed and the reaction temperature is in the range of about $+10°$ C. to about $-35°$ C.

7. The process of claim 6 wherein the reaction temperature is in the range of about $0°$ C. to about $-35°$ C.

8. The process of claim 1 wherein the amount of sulfuric acid employed is such as to provide at least two mols of hydrogen sulfate per mol of acetaldehyde.

9. The process of claim 1 wherein isobutylbenzene is chloroethylated by reacting it with hydrogen chloride and acetaldehyde at a temperature in the range of about $-10°$ C. to about $-35°$ C. in the presence of at least two mols of hydrogen sulfate per mol of acetaldehyde.

10. The process of claim 1 wherein isobutylbenzene is bromoethylated by reacting it with hydrogen bromide and acetaldehyde at a temperature in the range of about $0°$ C. to about $-35°$ C. in the presence of at least two mols of hydrogen sulfate per mol of acetaldehyde.

* * * * *